United States Patent [19]

Singer

[11] Patent Number: 5,843,794
[45] Date of Patent: Dec. 1, 1998

[54] TECHNIQUE FOR THE PREVENTION OF FALSE POSITIVE REACTIONS IN IMMUNOLOGICAL TESTING DUE TO $C_1$ AND $C_{1Q}$ COMPONENTS OF THE COMPLEMENT AND METHOD FOR SCREENING FOR RHEUMATIC FACTOR

[75] Inventor: Jacques Singer, Delray Beach, Fla.

[73] Assignee: Montefiore Medical Center, Bronx, N.Y.

[21] Appl. No.: 564,895

[22] Filed: Nov. 29, 1995

Related U.S. Application Data

[63] Continuation of Ser. No. 14,549, Feb. 8, 1993, abandoned, which is a continuation-in-part of Ser. No. 857,764, Mar. 26, 1992, abandoned.

[51] Int. Cl.⁶ .................................................. G01N 33/546
[52] U.S. Cl. ........................... 436/534; 435/7.1; 435/962; 436/541; 436/506; 436/175; 436/821; 436/825
[58] Field of Search .................... 435/7.1, 810, 962; 436/534, 541, 175, 821, 823, 825, 506

[56] References Cited

U.S. PATENT DOCUMENTS 4,062,935 12/1977 Masson et al. .............................. 424/12

OTHER PUBLICATIONS

Bormer, O.P. Journal of Immunological Methods 121: 85–93 1989.

Linker, III et al "Tests for Detection of Rheumatroid Factors" pp. 759–761 in *Manual of Clinical Laboratory Immunology*, ed Rose et al ASM1986.

Johnson, AM. "Immunoprecipitation in Gels" pp. 14–24 in *Manual of Clinical Laboratory Immunology*, ed Rose et al. ASM 1986.

European Journal of Clinical Chemistry and Clinical Biochemistry, vol. 29, No. 8, 1 Aug. 1991, Borgue, et al pp. 521–527.

Tohoku Journal of Experimental Medicine, vol. 146, No. 4, 1 Aug. 1985, Sendai Jp, pp. 449–456, K. Fukuda et al.

*Primary Examiner*—Carol A. Spiegel
*Attorney, Agent, or Firm*—Hedman, Gibson & Costigan, P.C.

[57] ABSTRACT

A novel technique is disclosed for the prevention of false positive reactions in immunological testing which are caused by interference of $C_1$ and $C_{1q}$. The method is based on heating a sample of a body fluid at a temperature of 59°–64° C. in the presence of a particular neutral salt. A method for screening for rheumatoid factor is also disclosed.

12 Claims, 3 Drawing Sheets

TECHNIQUE FOR THE PREVENTION OF FALSE POSITIVE REACTIONS IN IMMUNOLOGICAL TESTING DUE TO $C_1$ AND $C_{1Q}$ COMPONENTS OF THE COMPLEMENT AND METHOD FOR SCREENING FOR RHEUMATIC FACTOR

This application is a continuation of Ser. No. 08/014,549, filed Feb. 8, 1993, which is a continuation-in-part of Ser. No. 07/857,764, filed Mar. 26, 1992, both of which are now abandoned.

Throughout the specification and claim of this invention words and terms will be used which have the following meanings:

Particle Reagent

A direct inhibitor of agglutination in tests utilizing latex particles, charcoal particles, bentonite particles when the antigen or antibody are bound to the surface of particulate carrier by physical absorption or covalent chemically bound to measure antibody or antigen in human or animal fluids (blood, spinal fluid, CSF, ascitic, urine, etc.). Manual and instrumental kits being available for this technique.

Latex Fixation Test

An agglutination reaction in which latex particles are used to passively adsorb soluble protein and polysaccharide antigen.

Immunofluorescent

A technique for the detection and localization of antigens in which specific antibody is conjugated with fluorescent compounds, resulting in a sensitive tracer that can be detected by fluorometric measurement.

Immunoassay

A ligand binding assay which employs a specific antigen or antibody capable of binding to the analyte. Analytes are the substance, set of substances or factors to be assayed.

Radioimmunoassay

A variety of immunologic techniques in which a radio-isotope is used to detect antigens or antibodies in some form of an immunoassay.

Ouchterlony Double Diffusion

An immunoprecipitation technique in which antigens and antibodies are allowed to diffuse toward each other and form immunocomplexes in agar.

ELISA

ELISA enzyme-linked adsorbent when one immunoreagent can be immobilized on the carrier surface while retaining its activity and the reciprocal immunoreagent can be linked to an enzyme in such a manner that both the enzymatic reactivity and the immunoreactivity of this conjugate are retained.

Capillary Enzyme Immunoassay

Immunoassay reaction occur within glass capillary tubes, polyvinylchloride tubes and between small glass or clear plastic plates.

Particle Capture Assay (Enzyme Based Color Generating Immunoassay)

Latex particles are captured on filters, either by physical entrapment or by chemical adhesion to the filter fibers or capturing latex particles in suspension.

Dot Immunobinding Methodology

In this assay the capture reagent is bound to a microporous membrane and the specimen containing the analyte is allowed to flow over and around the capture reagent conjugate binding and color development in the DIB assay occurs as described for particle capture assay (immunofiltration assay).

Co-agglutination Test

Protein A rich cells of Staphylococus aureus bind immunoglobulins from many animal cells, and these antibody coated cell are use in agglutination reactions.

Complement Fixation

A standard serologic assay used for the detection of an antigen-antibody reaction in which complement is fixed as a result of the formation of an immune complex.

Antiglobulin Test (Coombs Test)

A technique for detecting cell bound immunoglobulin.

Immunoglobulin

A glycoprotein composed of (heavy) H and (light) L chains that function as antibodies immunoglobulin class. A subdivision of immunoglobulin molecule based on unique antigenic determinant in the Fc region of the heavy chain H chains. In humans these are 5 classes of immunoglobulin designated IgG, IgA, IgM, IgD and IgE. IgG is the predominant immunoglobulin class present in serum.

IgM

A pentameric immunoglobulin comprising approximately 10% of normal human serum immunoglobulin with a molecular weight of 900,000 and a sedimentation coefficient of 19 S (Svedberg units).

Fab

An antigen binding fragment produced by enzymatic digestion of an IgG molecule with papain.

F(ab')$_2$

A fragment obtained by pepsin digestion of immunoglobulin molecule. It contains antigen antibody activity. An F(ab')$_2$ fragment and an Fc fragment comprise an active monomeric immunoglobulin molecule.

Fc Fragment

A crystalizable fragment obtained by papain digestion of IgG molecule it contains antigen binding capacity.

Attenuation

When a serum sample shows reaction in a complement-fixation test but no reaction in an agar gel diffusion test is not detected after 24 hours but is detected after 48 hours.

BACKGROUND OF THE INVENTION

The diagnosis of certain diseases caused by pathogens such as bacteria or viruses is based in part of the detection of changes in the body's immune system. These changes are manifested by the detection of antibodies which are produced by the body in response to the protein-glycoprotein-polysaccharide constituents of the bacteria, viruses and parasites.

It is well known that when an antibody molecule is combined with a variety of specific antigenic determinants, an antibody-antigen reaction takes place. Specificity refers to the degree to which the antibody recognition of its antigen is unique. Many body fluids contain factors, largely undefined, which gave false positive or false negative results in an antigen-antibody test system.

The term antibody is commonly used to describe the substance gamma globulin which is present in serum, spinal fluid and other fluids. Antibodies identified as IgG, IgA, IgM, IgD and IgE are complex proteins or glycoprotein molecules. They are elaborated by the immune system in response to antigenic stimulation. Most known antigens are multivalent in that they have more than one combining site (or antigenic determinants) to which antibody may be bound.

The precipitin reaction is basic to immunology and immunochemistry because it permits the detection and quantitation of antigen and antibody in solution, in tissues, in individual cells or in region of cells.

Techniques used for detection and quantitation of antigen or antibody include radioimmunoassay, enzyme linked immunosorbent assay (ELISA), precipitin in tubes or by turbidimetry, light scattering, fluorescence immunoassay, precipitation on nylon or on paper membranes dot or blot assay, chromatography, neutrophil and platelet assays, acquired inhibition to clotting proteins, detection of antibody to tissue specific antigen and HLA typing, antiglobulin tests, immunodiffusion (double Ouchterlony, counterimmunoelectrophoresis, immunoelectrophoresis), complement fixation, DNA Probe immunology and the like. Agglutination techniques are based on the use of particles (latex, charcoal, bentonite, sheep cell, etc.); on slides, in test tubes, and/or on paper or utilizing instrument particle enhanced immunoassay; light scattering assay, particle counting assay, turbidometric assay and spectroscopic assay, Petinia assay, PACIA assay, Quels instrumentation assay, and the like.

Most of these assays are for measuring antigen antibody reactions for bacterial, viral, parasitic and fungal antigen and antibodies, immunoglobulins, hormones, drugs, tumor antigen and serum proteins.

False positive results may be caused by the presence in all sera of $C_{1q}$ which is a subcomponent of the $C_1$ complex. False positive results may also be caused by the presence in a large number of sera of rheumatoid factors (RF). False negative results may be caused by the presence of the undissociated $C_1$ complex.

The first component of the complement $C_1$ is largely dissociated under physiological conditions. The $C_1$ complement is composed of three subcomponents known as $C_{1q}$; $C_{1r}$; and $C_{1s}$ which are held together in a calcium dependent complex. $C_1$ when diluted with glycine buffer, pH 8.2 and/or when treated with EDTA-Na will dissociate into the three components ($C_{1q}$, $C_{1r}$ and $C_{1s}$). In the prior art, the $C_{1q}$ component was considered to be a thermolabile substance that could be inactivated by heat at 56° C. for 30 minutes. The present inventor has discovered that $C_1$ and $C_{1q}$ are only attenuated and not inactivated by heating a serum sample to 56° C. for 30 minutes. It was known in the prior art that $C_{1q}$ will react with gamma globulin in solution to agglutinate uncoated latex particles or latex particle coated with gamma globulin. $C_{1q}$ has binding sites for IgG and IgM and initiates the activation of the classical pathway cascade. The binding sites for $C_{1q}$ are located on the Fc portion of IgG and IgM. These binding sites are made up of known sequences of amino acids and the binding sites are sensitive to high ionic strength salts which is suggestive of electrostatic interaction. The binding between $C_{1q}$ and immunoglobulin is known to be inhibited by inorganic ions and organic ions in concentrations of 100–300 mM.

The following is the role of $C_{1q}$ in the body:

1. Interacts with immunoglobulin through the Fc fragment.

2. $C_{1q}$ forms an ionic bond and links many antibodies to their antigenic surface.

3. It stabilizes antigen antibody complexes.

4. It acts as a receptor for macrophages. It is through these receptors that AgAb complexes are phagocytized.

These components interfere in all immunoassay procedures by one or more of the following reactions: nonspecific agglutination of particulate carriers (latex, sheep cells, bentonite, charcoal); by interacting nonspecifically with endogenous immunoglobulin or with immunoglobulins of the antiserum added as a test reagent; by the inhibition or the amplification of many serological reactions; and by generating grossly abnormal analyte level.

$C_{1q}$ in human sera is capable of binding to antigen antibody complexes and to immunoglobulins such a IgG and IgM. The normal concentration of $C_{1q}$ is 70 mcg./ml. It will also bind to aggregated gamma globulin, will precipitate gamma globulin from solution as well as in agar gel systems. $C_{1q}$ binds to bacteria, bacterial lipopolysaccharide, dextran, heparin, polyinosinic acid carrageenan, DNA, C reactive protein, fibronectin, mitochondria, platelets, lymphocytes, monocytes, null cells, monosodium urate crystals, cytoskeletal filaments hybrid monoclonal mouse antibodies. $C_{1q}$ will bind or adsorb on glass, paper, plastic, etc.

Specific examples of particles which will bind $C_{1q}$ include synthetic polymeric particles of various chemical composition such as polystyrene, polyvinyl toluene, styrenebutadiene, styrene-acrylic acid and the like. The particles will react with $C_{1q}$ alone or when coated with anyone of the following: immunoglobulin, aggregated immunoglobulin, antigens, specific antibodies, sheep cell sensitized with coated anti-rabbit sheep cell antiserum.

When $C_{1q}$ is used as an exogenous reagent, to detect and quantitate antigen-antibody complexes which are present in certain diseases such as lupus erythematosus, rheumatoid arthritis, lyme arthritis, acute hepatitis, etc., erroneous results may occur because of interference with the endogeneous $C_{1q}$ and endogeneous immunoglobulin. Examples of the tests in which $C_{1q}$ is added are $C_{1q}$ binding assay, $C_{1q}$ solid phase assay, $C_{1q}$ inhibitory assay, $C_{1q}$ enzyme linked immunosorbent assay (ELISA), $C_{1q}$ AgAb assay (ELISA), $C_{1q}$ cocktail assay, ($C_{1q}$ bovine conglutin in and low affinity rabbit IgM antihuman Fc fragments) radioimmunoassay, $^{125}IC_{1q}$ PEG precipitation test.

It will be shown herein that $C_1$ and $C_{1q}$ under certain conditions can cause disaggregation or solubilization of AgAb of heat aggregation of gamma globulin.

The classic methodology for inactivation of complement involves heating samples to 56° for 30 minutes. Repeated freezing and thawing of sera may cause aggregation of gamma globulin. The aggregated gamma globulin will bind $C_{1q}$ thereby decreasing the activity of the complement. This property of the aggregated gamma globulin is called the anticomplementary property.

Heating serum at 56° for 30 minutes has been shown to be ineffective as a procedure for the inactivation of $C_{1q}$. The present inventor has discovered that only when the temperature is raised to 59°–64 C. for about 3 to 30 minutes in the presence of organic or inorganic ions, the $C_1$ and $C_{1q}$ are inactivated. The higher the temperature the shorter will be the required heating time.

It has also been discovered that heating a serum sample at 59°–64 C. for about 3–30 minutes prevents the interference of the complement in immunoassays even though heating at 56° C. for 30 minutes reversibly attenuates the complement.

The effect of heat at temperatures of 56° C.; 59° C.; 61° C. and 64° C. was demonstrated by heating human gamma globulin (HGG) in a glycine buffer (buffer #2 as described herein) at a concentration of 18 mg/ml for various times. The degree of aggregation was determined in a photometer by reading the optical density of different samples at 5 minute intervals depending on the amount of aggregation obtained. The results are reported in Table I which shows that as the temperature is increased from 56° C. to 64° C. over a period of time the amount of aggregation increases by a factor of about forty. It is unobvious to use a temperature of more than 56° C. to treat any test sample containing IgG because it has been demonstrated that higher temperature cause self-aggregation of IgG and would interfere in a photometric assay. This is evidence that it is unobvious to use a temperature range of more than 56° C. for treating a sample before subjecting it to an immunoassay. It is only when a neutral salt is added to a sample of body fluid that it is possible to utilize the temperature range of 59°–64° C. to inactivate the complement without causing increased self-aggregation of IgG.

TABLE I

| Minutes | 56° C. OD | 59° C. OD | 61° C. OD | 64° C. OD |
|---|---|---|---|---|
| 5 | 0.0362 | 0.0038 | 0.0458 | 0.0962 |
| 10 |  |  | 0.0969 | 0.8359 |
| 15 | 0.0362 | 0.0605 | 0.124 | 1.15 |
| 20 |  | 0.0706 | 0.2219 |  |
| 30 | 0.0555 | 0.1248 | 0.5229 |  |
| 60 |  | 0.3979 | 0.8539 |  |

When antibodies are attached to the surface of a solid state immuno test, they will aggregate on the surface and will interfere with antigen-antibody reactions. A further example of complement interference is when normal sera are added to a solid state immunoassay as a blocking agent. The normal sera contains $C_1$ and $C_{1q}$ which will bind non-specifically to AgAb complexes or it may dissociate and solubilize AgAb complexes in the test sample.

$C_{1q}$ will compete for binding sites with collagen and will bind to the platelets causing adhesion, aggregation and serotonin release.

The practical problem which results from the interference of $C_{1q}$ is the false negative results when the presence of antibodies is masked or an increase or decrease in the quantitation of the antigen or antibody reaction causing an alteration of assay sensitivity or accuracy.

A large number of methods have been used in the prior art to eliminate $C_{1q}$ in immunoassay procedure. These methods include:

1. Use of antisera to $C_{1q}$ which is intended to neutralize exogenous and endogeous $C_{1q}$.

2. Use of dilution of serum to minimize the amount of endogenous $C_{1q}$.

3. Inactivation of $C_{1q}$ by heating the sample to 56° C.

4. Heating sample containing $C_{1q}$ to 56° C. in the presence of O.1M EDTA Na.

5. Use of control solid adsorbent with non-immune antibodies.

6. Use of aggregated gamma globulin to trap and bind the endogenous $C_{1q}$.

7. In the latex test, the gamma globulin to be adsorbed on the surface of latex is replaced with a fragment of the same antibody $F(ab')_2$ fragment for coating latex particle. $C_{1q}$ binds to Fc fragment of immunoglobulin but not to the $F(ab')_2$ fragment.

8. To eliminate nonspecific agglutinator for latex, CSF is boiled at 100° C. for five minutes or urine is heated at 100° C. for 3–5 minutes. Following heat treatment urine or CSF are centrifuged and the supernatants are tested.

9. In a test for antigen antibody complexes, a euglobulin from fraction is used which is obtained from ascitic mouse fluid.

None of these methods have completely prevented the interference that is caused by $C_1$ or $C_{1q}$.

It was known in the prior art that certain chemical compounds could inhibit the reaction of $C_{1q}$ and immuno-globulin. It was surprising and unexpected that the chemical compounds such as the inorganic salts which were previously known as inhibitors of the $C_{1q}$-IgG or $C_1$-IgM reactions were found by using the latex photometry technique to be activators of $C_1$ by unmasking the $C_{1q}$ agglutinator.

Therefore, it is a primary object of this invention to provide an improved method of eliminating false positive and false negative results that are caused by one or more components of the complement system $C_1$ and $C_{1q}$.

It is also an object to provide a method of neutralizing or inactivating the interference of the complement in immunoassay testing.

It is also an object of the invention to provide novel test kits which include novel reagents for use in all immunoassay procedures.

It is also an object of the invention to provide a method for preventing the formation of aggregates of immunoglobulin in sera.

It is also an object of the invention to provide a method for the prevention of the aggregation of gamma globulin by heat at a temperature of 59°–64° C. in the presence of a neutral salt for a period of 3–30 minutes depending on the temperature.

It is also an object of the invention to provide a technique for the recognition of $C_{1q}$ in sera by the use of heat at a temperature of 59°–64° C. in the presence of a neutral salt for a period of 3–30 minutes depending on the temperature.

It is also an object of the invention to provide a technique for the detection of rheumatoid factor in sera by the use of heat at a temperature of 59°–64° C. for an effective period of time in the presence of a neutral salt and latex coated with gamma globulin.

It is also an object of the invention to provide a technique for the quantitative measurement of rheumatoid factor.

It is also an object of the invention to provide a technique for the quantitative measurement of $C_{1q}$ purified protein.

It is also an object of the invention to provide a method of inhibiting aggregated gamma globulin or antigen-antibody complexes that have not been denatural by heat.

It is also an object of the invention to provide a novel apparatus for the automated performance of immunoassays.

SUMMARY OF INVENTION

The invention comprises a method for the prevention of the interfering effect of $C_1$ and $C_{1q}$ from a body fluid in immunoassays, said method comprising the steps of:

(a) adding an effective amount of a chemical compound to a diluted sample of a body fluid, said chemical compound being capable of inactivating the $C_1$ or $C_{1q}$ in said body fluid when a mixture of said body fluid and said chemical compound are heated to a temperature of 59°–64° C. for a sufficient period of time to inactivate said $C_1$ or $C_{1q}$ without affecting the reactivity of the antigen or antibody in said body fluid; and (b) heating the diluted sample containing said chemical agent and said body fluid to a temperature of about 59° C. to about 64° C. for a period of time which is sufficient to prevent the interference of $C_1$ and $C_{1q}$ in immunoassays.

In a useful procedure for the practice of the invention, a 0.25 ml of the sample which is to be tested in an immunoassays procedure, is diluted 1:10 in glycine buffer, pH 7.8–8.2, ionic strength 0.025–0.0125. Then, 20 µl of a solution of a neutral salt (2M NaCl or 2M KCl or 0.1M EDTA-Na) is added to the diluted body fluid is incubated at 63° C. for 3 minutes. If the sample is to assayed for RF, the preferred temperature is 60° C. for 30 minutes.

The invention also includes the screening method which uses latex particles to determine if a sample of a body fluid, i.e. sera, synovial fluid, pleural fluid or ascitic fluid contains $C_{1q}$ or RF using a sequence of steps which are based on the reactivity of $C_{1q}$ and RF with latex particles and the use of heat in the presence of a suitable chemical compound, as herein defined, to inactivate $C_{1q}$. A screening method has also been devised for the demonstration of the presence of $C_{1q}$ by the Ouchterlony technique has been devised.

The invention further includes the method for the detection and semiquantitive determination of RF in human sera and fluid by the use of heat and a suitable chemical compound which is used to prevent interference caused by $C_{1q}$ to make the latex test specific for RF.

A technique has also been devised for the determination of the amount of purified $C_{1q}$ using latex particles.

The invention also provides a novel apparatus for automatically carrying out latex agglutination tests without interference from $C_{1q}$ or RF.

DETAILED DESCRIPTION OF THE INVENTION

The term "body fluid" includes cerebrospinal fluid, synovial, ascitic fluid, pleural fluid, blood and the like, urine and serum. When these materials are tested, the interferring effect of $C_1$ and $C_{1q}$ in an immunoassay may be prevented by the methods set forth herein. The preferred detection method for use in demonstrating the operability of the invention is the photometric latex agglutination technique.

The photometric latex agglutination technique is a simple, rapid, qualitative and quantitative immunological assay. It can be performed in minutes with small quantities of reagents. The sensitivity can be adjusted over a wide range and it can quantitate as little as 10 nanograms of antigen and antibody. A photometer which may be used for latex agglutination is a Model 500 (Chronolog Corp.) used for blood Aggregometry. The instrument is provided with temperature controls and the heater block is controlled to 37° C. It has a stirring motor with a stirring speed at 1200 rpm.

The reaction between the latex antigen and antibody mixture is performed in a single tube with continuous stirring and then measured by monochromatic light transmitted through the suspension which is undergoing continual flocculation. Flocculation is measured by monitoring the changes in transmission as a function of time using a single channel recorder connected with the aggregometer. The difference in light transmission is expressed as a voltage and recorded as in function of time. The ensuing flocculation is evidenced by a change in transmission (T) with time (t). The variation of % transmission with time is a measure of the rate of changes of particle size during flocculation. The increase in transmission is a result of the $0.8\mu$ size latex particle colliding during AgAg reaction and forming larger and fewer aggregates of latex particle up to $5-6\mu$ in diameters. When it reaches the maximum size, the sigmoidal flocculation curve become asymptotic. The point in flocculation when the particle size changes most rapidly is represented by the slope of the percent transmission curve. This slope is measured with a tangent meter within a few minutes after the latex suspension is added. In the use of negative fluid where no antigen antibody reaction takes place, the transmission versus the time will result in a straight line. The maximum slope value is detected in less than 3 minutes. To obtain quantitative information, the sera are diluted and each aliquot is run in the photometer. A family of curves for serum samples of different dilutions is then obtained and the slopes are calculated. A standard curve is generated by plotting the maximum slope response of the various dilutions of the fluid containing a certain amount of antigen or antibody. The curves for the unknown samples are compared to the standard curve and the quantitative estimation is based on the comparison.

Figure 1:
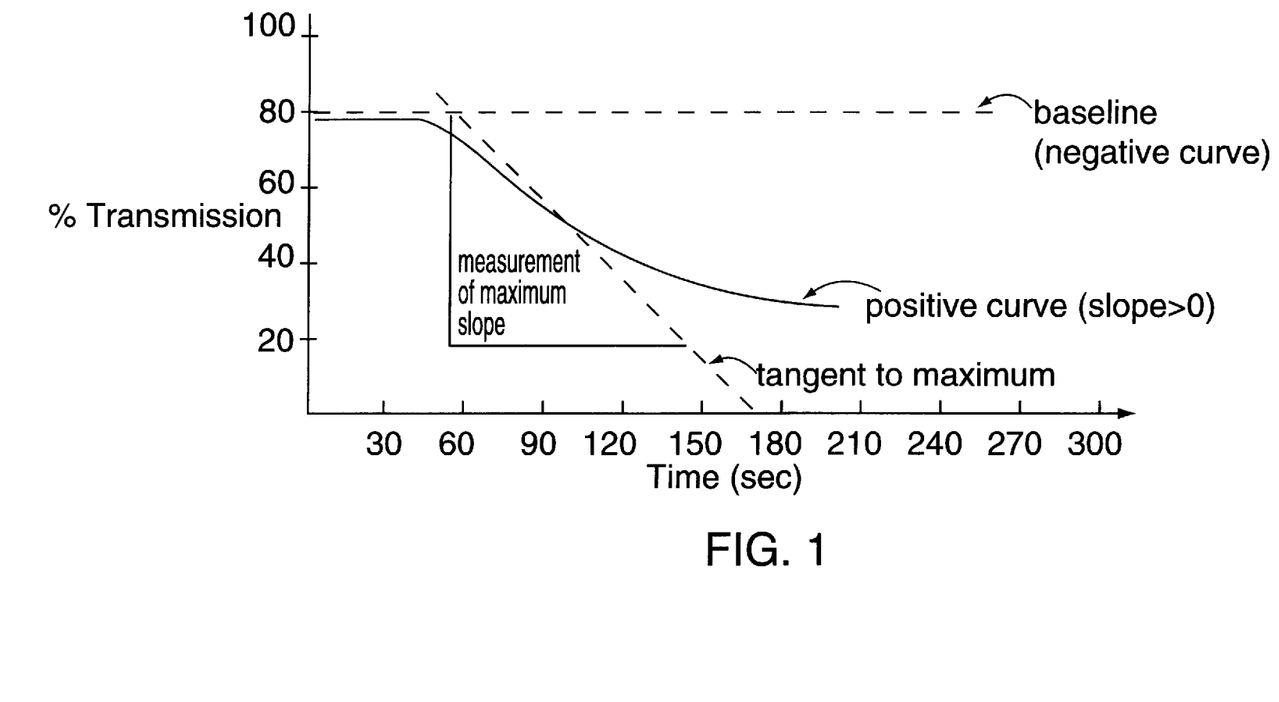
FIG. 1 is a graph which illustrates a plot from an X-Y recorder of a photometer which shows both a baseline (negative curve) of a negative turbidometric test and a positive curve (slope >0) of a positive turbidometric test. The dashed line marked "tangent to maximum" is the line drawn with a tangent meter to measure the maximum slope as shown by the superimposed right triangle marked "measurement of maximum slope".

A typical base line or negative curve which is actually a substantially straight line is shown by the horizontal dotted line and a positive "curve" is shown in FIG. 1. The dotted line is a line which is drawn on a tangent to the sigmoid shaped curve at a point on the curve where the slope is at a maximum as recorded by the X-Y plotter. The maximum slope is the region where the rate of change of the particle size of the flocculating particles is the greatest.

It is possible to predict from the standard curve the results for any dilution of a body fluid without testing the unknown body fluid at several dilutions.

The preferred chemical compounds for use in the practice of the invention include the neutral salts of the Hofmeister series, organic acid salts or diamino compounds. Any of these compounds may be used in the practice of the invention provided that when they are added to a 1:10 dilution of a sample of a body fluid in a glycine buffer pH 7.0–8.5, pH 8.2, and a ionic strength of $0.0125-0.025\mu$ at a concentration of 40 mM to 200 mM, and the sample is heated to a temperature of 59°–64° for a sufficient period time, e.g. from 3 to 30 minutes, the interference of $C_1$ or $C_{1q}$ is prevented without affecting the reactivity of the antigen or antibody in said body fluid.

The following is the list of salts which have been shown to be promoters of the latex agglutination test. In addition to unmasking the $C_{1q}$ these salts will neutralize the charged group of the $C_{1q}$ and also serve to dissociate the $C_{1q}$ complexes from immunoglobulin and AgAb complexes:

TABLE A

| Inorganic ions |
|---|
| sodium bromide |
| sodium chloride |
| sodium iodide |
| sodium citrate |
| sodium cyanate |
| sodium perchlorate |
| sodium acetate |
| Organic ions |
| ethylenediamine sodium |
| ethylenediamine tetraacetic |

TABLE A-continued acid tetrasodium
sodium propionate
sodium butyrate
1,4 diamino butane
suramin
heparin Other neutral salts of the Hofmeister series which inactivate the $C_1$ or $C_{1q}$ when heated to a temperature of 59°–64° for a sufficient period of time may also be utilized.

The neutral salts are strong electrolytes serving as a source of ionic strength. The charge of a neutral salt influences the macromolecular confirmation by weakening attractive or repulsive inter and intra-charge=charge interaction. Therefore, reaction with charge residues, the reaction with dipolar groups such as peptide bond, amino, carboxyl, hydroxyl, primary and tertiary amide, it will alter the free energy difference between folded (associated) and unfolded (dissociated) form of the macromolecule neutral salt exercising striking effects on association and dissociation equilibria. It should be noted that EDTA $Na_4$ is used herein for its action as a neutral salt and not for its chelating or complexing properties.

Large numbers of studies have dealt with the effect of neutral salts on a protein. Tandford, C. Physical Chemistry of Macromolecules, Wiley, N. Y. C., Chapter 8. Herskovitz, T. T. and Kely, T. M. J. Physical Chemistry 77:381, 1973.

While the exact mechanism for the reaction is not known, it is believed that it is these neutral salts which are used in this invention function as an activator to unmask and release the $C_{1q}$ component of the $C_1$ complex and of the serum. The same neutral salt will be used to dissociate $C_{1q}$ from complexes with IgG, IgM and AgAb complexes and finally will also be used by heat to inactivate the $C_{1q}$ components.

Protein interaction is a complex process in which shape, electrostatic potential and hydrophobicity and hydrophilicity of the interacting molecules plays a role. Stability of IgG as well as of all proteins depends greatly on factors such as hydrogen bonding, hydrophobic bonding, van der Waals interaction, electrostatic forces of attraction and repulsion among charged surface and bound water. Therefore, the effect of salts on $C_{1q}$ and immunoglobulins or on any protein will depend on the salt effect on these stabilizing factors.

Because of the many stabilizing factors which exist, the salts will affect the protein molecule through different mechanisms, P. H. Hippel and T. Schleigh pp. 417–574 in Structure and Stability of Biological Molecule. Ed. S. N. Timasheff and G. D. Fishman, Marcel Decker, N. Y. 1969.

The inorganic and organic salts exert a structural perturbance on protein. They modify the environment of a macromolecule and thus affect the way they operate in aqueous solution through temperature, pH, compete hydrogen bonding, hydrophobic bond effectors. Neutral salts are defined as strong electrolytes which are significantly soluble in water without imparting major charge to in solution pH. The mechanism by which neutral salts or aliphatic acids act on proteins, in association and dissociation of large protein has been postulated. The first mechanism is through reaction with charged residue. Since the charges of the proteins are mostly located at the surface of the macromolecule they should not have a major effect on the residue located inside the macromolecule.

The second mechanism is the reaction with dipolar groups in the macromolecule such as the peptide bond, amino, carboxyl and hydroxyl groups, primary, secondary and tertiary amino groups, etc.

The third mechanism is the non-polar interaction. These are compounds which are partially by non-polar or hydrophobic in character.

The fourth mechanism is organic salts are added to the protein, both intra and intermolecular bonds are broken, the side chains of the molecule are exposed and the water (or the solvent) alters its structure to make it thermodynamically hospitable for the newly exposed non-polar group.

It is recognized that heating sera at 53° C. and higher will aggregate gamma globulin.

Since $C_{1q}$ binds strongly or complexes with aggregated gamma globulin, the present invention provide the novel methodology which is based on the use of heat and an inorganic or organic anion to produce a change in the configuration of immunoglobulin and bind $C_{1q}$ without producing a degree of aggregation which will irreversibly bind the $C_{1q}$ to the aggregated immunoglobulin.

The mechanism by which heat in the presence of a neutral salt prevents the interference of $C_{1q}$ in an immunoassay can be postulated as follows:

1. $C_{1q}$ is released from the $C_1$ macromolecular complex; released from the binding site of $C_{1q}$ with IgG, IgM, IgGIgM and IgGIgG complexes or from the $C_{In}$ inhibitor and other binding sites by:

a. dilution of serum with low ionic strength buffers such as glycine, borate and phosphate buffers;

b. addition of inorganic or organic neutral salts which affect the binding sites of $C_{1q}$ with immunoglobulins or antigen-antibody complex or $C_1$ inhibitor;

c. use of heat to produce an unfolding or a conformational change in the molecule of immunoglobulin for a greater capacity of fixing $C_{1q}$; and    d. prevention of heat aggregation of immunoglobulin by the solubilizing or inhibiting effect of $C_1$ and $C_{1q}$ and a neutral salt.

$C_{1q}$ which is released in soluble form by heat in the presence of salt, is inactivated by heat and it is prevented from interferring in immunological reaction.

It appears that in the heating process hydrogen bonds are broken down between the oxygen atom of carboxylic acid groups and hydrogen atoms of amino groups. Heating at 60° C. for longer periods of time causes protein molecules to unfold. The neutral salts which have electrostatically neutralized the charged group of $C_{1q}$ will inactivate the $C_{1q}$ molecule. Alteration of the binding sites of $C_{1q}$ will prevent $C_{1q}$ from agglutinating or binding with immunoglobulin. False positive (nonspecific) results which are due to $C_{1q}$ in immunoassay are thereby prevented.

The latex fixation test is positive for 75–80% of rheumatoid patients, and is also positive in 0–25% of patient with other diseases. Approximately 25% of all sera positive patients who have RA have a titer between 1:160–1:640. Singer and Plotz have suggested that a titer of 1:80 or more should be considered positive. As stated in the proficiency testing for RF, by the Communicable Disease Center, many laboratories report as significant a titer higher than 1:80. It was suspected that the false positive tests were due to the presence of $C_1$ or $C_{1q}$ in sera. This is the reason for false positive results in which low titers cannot be defined for RF sera and probably the reason that only 80% of RA patients have a positive test. Furthermore, in many clinical situations $C_{1q}$ may be increased in sera and cause a positive test result for RF. The clinical significance of a positive test and different titers are confusing. Physician interpretation, in many instances, is made without knowledge of the interferences of $C_{1a}$ or $C_1$ in serological testing.

It is for this reason that this invention eliminates the $C_{1q}$ interference and any titer which obtained in the latex gamma globulin slide, tube or nephelometric test would be only due to the presence of RF.

The prevention of the $C_{1q}$ interference makes it possible to assign a meaningful titer to the RF test which can be correlated with clinical symptomology.

For the detection or quantitation of rheumatoid factor in the latex photometric technique, it is preferred to prepare a sample by adding a chemical compound as hereinabove described to a diluted body fluid and apply heat at a temperature of 60° C. for a period of about 30 minutes although higher temperatures, i.e., 63° C. for a shorter period of time, i.e., 3 minutes could be utilized. Thereafter, the prepared sample is tested for the presence of RF by contacting the sample with coated or uncoated latex particles.

Any agglutination of the latex particle may be rapidly detected visually or in a spectrophotometer. The optical density of the sample increases in direct relation to the amount of RF in the sample. After standardizing the spectrophotometer by using a reference standard sample of RF, the sample is placed in the spectrophotometer and if a flocculaton curve is observed within three minutes, the sample is positive for RF. This method has the advantage of providing physicians with rapid, sensitive and reproducible test results which are obtained from a sample that has been treated to eliminate any $C_1$ or $C_{1q}$ that might cause a false positive result. In addition, the fact that any interference due to the $C_1$ or $C_{1q}$ has been prevented makes possible the use of an automated spectrophotometer with a microprocessor controlled heater which prevented any error caused by subjective reading of a slide or tube test and provides a permanent printed record. This provides quality assurance and a record for proficiency testing for regulatory authorities. It should be understood that the $C_1$ component and RF bind to the same sites on the IgG molecule and therefore it is of primary importance that the $C_1$ component be inactivated. This will eliminate the possibility of false negative results which would be caused by $C_1$ binding at the sites where RF must bind to form agglutinated IgG. This also reduces the sensitivity of the test.

If quantitative test data is required, the sample which has been qualitatively tested is serially diluted. Each serially diluted sample is tested in the spectrophotometer to obtain a curve until the point when a serially diluted sample does not give a curve. The titer is the dilution of the most dilute sample which yields a curve.

If quantitative data is required, a series of reference standard curves in a photometer are prepared using known amounts of purified RF or standardized rheumatoid factor serum which is free of $C_{1q}$ and coated latex particles. The reference standard curves are compared to the curve for the test sample to determine the quantity of RF present in the sample.

The following latex immunoassays are examples of the tests which may utilize the present invention:

TABLE B

Bacterial Infection:

Brucella
Campylobacter jejuni
Cholera toxin

TABLE B-continued

Clostridium difficile
Diptheria
Escherichia coli
Haemophilus influenzae, Type b
Klebsiella (six types)
Legionella
Leprosy
Leptospirosis
Mycobacterium tuberculosis
Neisseria gonorrhoeae
Neisseria meningitidis (dif. groups)
Pneumococcal infection
Pseudomonas
Proteus (three types)
Salmonella (serological typing)
Shigella (serological typing)
Staphylococcus aureus
Staph. a. clumping factor, Protein A
Staph. enterotoxin A to E
Streptococcal Grouping A,B,C,D,E,F,G,Q
Streptococcus, Group A
Group B. Streptococcal (GBS) Antigen
B-hemolytic Strep., Groups A,B,C,G
Streptococcus pneumoniae
Syphilis/Yaws
Tetanus Toxoid
Tularemia
Whooping Cough
Yersinia pestis (plague)
Mycological Infection:

Actinomyces viscosus
Aspergillus fischeri
Candida albicans
Coccidioides immitis
Cryptococcus neoformans
Farmer's Lung
Histoplasma capsulatum
Sporothrix schenkii
Mycoplasma Infection:

Mycoplasma pneumoniae (various species
Parasitic Infection:

Amoebiasis (Entamoeba histolytica)
Canine Heartworm
Chagas' disease
Chlamydia
Filariasis (elephantiasis)
Hydatid disease (Echinococcus granulosus)
Kala-azar
Malaria
Toxoplasma gondii
Trichinella spiralis
Trichomonas vaginalis
Trypanosoma congolense
Rickettsial Infection:

Rickettsia conorii
Rickettsia prowazekii
Rickettsia rickettsii
Rickettsia typhi
Viral Infection:

AIDS
Avian encephalomyelitis
Cytomegalovirus (CMV)
Enterovirus
Hepatitis
Herpes
Infectious Mononucleosis
Measles
Pseudorabies in Swine (herpes)
Rotavirus
Rinderpest
Canine parvovirus
Rubella
Toga Viruses

TABLE B-continued

Autoimmune Diseases:

Anti-Nuclear Antibody
Rheumatoid Factor (RF)
Systemic Lupus Erythematosus
(Deoxynucleoprotein, DNP)
Thyroiditis
Hormone Assay:

Estriol ($E_3$)
Estrogen
Human Chorionic Gonadotropin (HCG)
B-subunit HCG
Human Growth Hormone
Human Placental Lactogen (HPL)
Thyroglobulin
Thyroid Antibody
Drug Assays:

Amikacin
Barbiturates
Cortisol
Digoxin
Gentamicin
Morphine
Netilmicin
Phenobarbital
Phenytoin
Primidone
Theophylline
Tobramycin
Others:

Allergy Testing
$Alpha_1$-Anti Trypsin
Alpha-Fetoprotein (AFP)
Anti-Microsome
Anti-NADase
Anti-Streptokinase
Anti-Streptolysin O (ASO)
Anti-Thrombin III
Anti-Thyroglobulin
Anti-Microglobulin
$B_2$-Microglobulin
Carcino-Embryonic Antigen (CEA)
Circulating Immune Complexes
Complement $C_3$ & $C_4$
C-reactive Protein (CRP)
Ferritin
Fibrin/Fibrinogen Degrad. Prods. (FDP)
Fibrinogen
Haptoglobin
Hemoglobin
Histamine
Human blood (forensic use)
Human semen (forensic use)
Immunoglobulin IgA
Immunoglobulin IgD
Immunoglobulin IgE
Immunoglobulin IgG
Immunoglobulin IgM
Lipase
Multiple sclerosis
Multi-Tumor Antibody (MTA)
Myeloid Leukemia
Myoglobin
Plasmin
Plasminogen
Sarcoidosis
von Willebrand Factor Antigen Two techniques were used to generate experimental data to demonstrate the application of this invention.

A. Latex photometric rate reaction as a representative of particulate immunoassay techniques.

B. Ouchterlony analysis to detect the reaction of antigen and antibody by the precipitation techniques. Immunoprecipitation is the simplest and most direct means of demonstrating antigen antibody reaction in the laboratory and can be applied to all other immunoassay procedures.

Since the present invention was developed using latex photometry, this procedure will be described first:

A. LATEX PHOTOMETRIC RATE REACTION TECHNIQUES

1. Glycine Buffer #1:
   Reagents: Glycine saline buffer. To 975 ml of 0.1M glycine add 2.5 ml of iN NaOH made up to 1000 ml with distilled water and the pH adjusted to pH 8.2 Ten gram of sodium chloride are then added to each 1000 ml buffer.
   Glycine Buffer #2:
   Dilute 100 ml glycine saline buffer to 700 ml of distilled water to make a 1:8 dilution of the buffer.
2. Latex particles: Seragen Diagnostic, Bang Laboratories, Indianapolis, Ind., Polystyrene latex 10 percent solid particle size $0.777\mu$ diameter.
3. Human gamma globulin PENTEX, 0.5 gr percent solution in glycine saline buffer #1.
4. Latex particles suspension is prepared by adding 25 $\mu$l of latex 10% particles size $0.777\mu$ diameter to 10 ml of glycine buffer #1.
5. Latex human gamma globulin suspension. To 10 ml glycine saline buffer #1 add 25 $\mu$l of latex 10% and 50 microliter of human gamma globulin.
6. EDTA tetrasodium 0.1M In the general procedure of the invention, sera or fluids to be tested are diluted in 1:10 glycine buffer # 2, to 0.25 ml of the diluted serum is added 10 $\mu$l of 0.1M EDTA tetrasodium dihydrate and incubated in a temperature controlled bath, at 59°–64° C. for 3–30 minutes. Thereafter, latex particle, coated with IgG or uncoated, are added and tested for the presence of flocculation or aggregation of the latex particles.

DESCRIPTION OF THE PREFERRED EMBODIMENT

The following examples are presented in order to illustrate the present invention. They are not to be construed to limit the scope of the appended claims.

EXAMPLE 1

This example describes a screening method to determine if a sample of a body fluid is RF positive or if it contains $C_{1q}$.

Sera is diluted to a dilution of 1:10 with glycine buffer #2. The diluted sample is placed in the Chronolog photometer with continuous stirring. To this sample is added 0.25 ml of a suspension of uncoated latex particles. If the recorder of the photometer shows a straight line it indicates that there is no detectable $C_{1q}$ and RF. If a sigmoidal curve is obtained, this indicates the the sample contains $C_{1q}$ or rheumatoid factor.

If in the sample which has been treated with latex particles, a straight line is still observed after three mintues, a neutral salt (10 $\mu$l 2M NaCl) is added to the mixture of sera and latex. If a flocculation curve is then obtained in the photometer, this indicates the presence of masked $C_{1q}$ or RF or a mixture of $C_{1q}$ and RF. If no flocculation curve is obtained, an aliquot of the sera, buffer, and 2M NaCl is prepared as described above. That mixture is heated at 56° C. for 30 minutes and uncoated latex is added. A flocculation curve should be observed, which indicates the presence of $C_{1q}$ and RF.

Whenever a flocculation curve is obtained, a new aliquot of the sera, buffer, and 2M NaCl is prepared and heated at 63° C. for 3 minutes; and uncoated latex is added. If a flocculation curve is observed, it confirms the presence of RF; if no flocculation curve is observed, it confirms that the sera is negative for RF and by inference, the specimen did contain $C_{1q}$.

This example represents a screening prodcedure for detection of RF if present in the body fluid, which also may be used to confirm that in a sample to be used in the immunoassay procedure, any interference which may be caused by $C_{1q}$ has been prevented.

EXAMPLE 2

This example demonstrates that the $C_{1q}$ subcomponent of the $C_1$ will agglutinate sera and is inactivated by 63° C. for 3 minutes in the presence of salt.

A commercial preparation of a $C_{1q}$ depleted human serum is tested with a latex IgG preparation in the photometer. No agglutination of latex particles take place when 0.25 ml of serum diluted 1:10 with glycine buffer #2 pH 8.2 is added to the latex IgG suspension. If 0.25 ml serum which is depleted of $C_{1q}$, is combined with 15 μl of purified commercial $C_{1q}$ preparation, the serum gives strong positive latex agglutination. Diluted sera was then heated at 63° C., for 3 minutes in the presence of 15 μl of 2M NaCl and when tested with latex coated with IgG, no agglutination was detected.

COMPARATIVE EXAMPLE

This example shows that IgG agglutinate with various purified complement components and with Rheumatoid factor with added $C_1$ or added negative serum when the sample is not treated with heat at 59°–64° C. for a sufficient period of time.

| Experiments |
| --- |
| 1. $C_1$, 20 μl in 0.25 ml of glycine buffer #2 |
| 2. $C_1$+EDTA-Na, added 10 μl of 0.1M EDTA-Na |
| 3. $C_{1q}$, 10 μl |
| 4. $C_{1r}$, 10 μl |
| 5. $C_{1s}$, 10 μl |
| 6. $C_1$ inhibitor, 10 μl |
| 7. Purified RF, 10 μl |
| 8. Purified RF + 10 μl $C_1$ |
| 9. Purified RF and 25 μl Negative serum. |

$C_1$ Diamedix 0.04 mg/ml; $C_{1q}$ Sigma 0.5 mg/ml;
$C_{1r}$ human 250 μg;
Calbiochem;
$C_{1s}$ Calbiochem 500 μg/ml;
RF purified 1 mg/ml;
$C_{1nh}$ 0.5/mg Calbiochem.

This table shows that $C_1$ (1), $C_{1r}$ (4), $C_{1s}$ (5), and $C_1$ inhibitor do not agglutinate latex IgG particles. When $C_1$ is treated with EDTA-Na it releases the $C_{1q}$ subcomponent which will agglutinate latex IgG particles. Purified RF preparation (7) agglutinates latex IgG, however, when $C_1$ is added to, purified RF (8) it inhibits the RF agglutination of negative sera containing the $C_1$.

EXAMPLE 3

This example shows that latex particles coated with HgG or uncoated can be used to detect the presence of $C_1$.

Latex particles uncoated or latex particles coated with human gamma globulin were added to purified $C_{1q}$ from Diamedix Corp., Sigma Lab, Behring, Atlantic Lab each in concentrations of 0.5 mg of $C_{1q}$/ml. All of these preparations agglutinated latex particles that were coated or uncoated with gamma globulin.

Dilutions of $C_{1q}$ were prepared from $C_{1q}$ obtained from Cytotec. These dilutions were quantitated in a photometer using the technique described above with uncoated latex particle. The results were as follows:

TABLE 2

| CONCENTRATIONS | |
| --- | --- |
| mg/ml | Mx Slopes |
| 0.5 | 1.2 |
| 0.025 | 0.60 |
| 0.0125 | 0.30 |
| 0.00625 | 0.18 |
| 0.003125 | 0.09 |
| 0.0015625 | 0.045 |
| 0.0007812 | 0.027 |
| 0.0003906 | 0.014 |

EXAMPLE 4

This Example demonstrates the effect of various concentrations of the neutral salts on normal sera which is heated at 60° C. for 30 minutes.

Various amounts of EDTA tetra sodium solution added to 0.25 ml of a negative serum, tested by the photometric technique with latex IgG.

TABLE 3

| 0.1M EDTA tetra Na μl added | Slopes Unheated | Slopes Heated at 60° C. |
| --- | --- | --- |
| 0 | 0.08 | 0 |
| 10 | 0.958 | 0 |
| 20 | 1.12 | 0 |
| 30 | 0.815 | 0 |
| 40 | 0.786 | 0 |
| 50 | 0.647 | 0 |
| 60 | 0.647 | 0 |
| 70 | 0.660 | 0 |
| 80 | 0.660 | 0 |
| 100 | 0.660 | 0 |

Normal sera whch is heated at 60° C. 30' in the presence of a neutral salt (EDTA-tetra Na) gives a negative reaction even though it previously gave a positive reaction when tested in the photometric technique with latex IgG.

A subsequent test using normal sera and the same concentration of EDTA tetra Na, using uncoated latex and heat at 63°±1° C. for 3' gave a zero slope for each concentration.

EXAMPLE 5

This example reports the testing of 100 normal donor sera by latex photometry.

TABLE 4

| | 1 Unheated* Percent | 2 Heated 56° C. 30' Salt Added Percent | 3 Heated 56° C. 30' No Salt Added Percent | 4 Heated 60° C. 30' Salt Added Percent | 5 Heated 63° ± 1° C. 3' Salt Added Percent |
| --- | --- | --- | --- | --- | --- |
| Nonspecific Agglutination | 20 | 100 | 100 | | |
| No Agglutination | 80 | | | 100 | 100 |

*control

One hundred samples of sera obtained from apparently healthy blood donors were first tested for the presence of rheumatoid factor by the slide technique (Rheumatex, Wampole Laboratories, Cranbury N.J. and the standard latex fixation test tube method of Singer and Plotz. Am. J. Med 21:888–892 (1956). The tests were negative for all sera.

Each serum was diluted 1:10 in gycine buffer #2 and treated as follows:
1. unheated, no salt added;
2. heated at 56° C. for 30 minutes and added 15 µl of 0.1M sodium EDTA;
3. heated at 60° C. for 30 minutes with no added salt;
4. heated 60° C. for 30 minutes with 15 µl 0.1M EDTA Na added; and
5. heated at 63°±1° C. with 15 µl 0.1M EDTA Na added.

The table shows that 80% of the unheated sera are negative by this procedure for $C_{1q}$, however, when heated at 56° C., 30' with or without salt, the sera become positive for $C_{1q}$. When these sera are heated at 60° C. 30' and 63°±1° C. 3' in the presence of EDTA Na these sera become negative for $C_{1q}$. The $C_{1q}$ from the normal sera which previously agglutinated latex particles at 56° C. become inactivated at 60° C. 30' or 63°±1° C. for 3' minutes only when heated in the presence of the salt.

The sera should not be treated at a temperature of 63°±1° C. without added salt because if a sample has a high level of gamma globulin i.e., more than 18 mg/ml, the high level of gamma globulin may cause aggregation.

EXAMPLE 6

This example shows the effect of salt and heat in RF containing sera.

Fifty rheumatoid sera were diluted in glycine buffer #1 to a dilution of 1:10 and tested unheated, heated at 56° C. for 30 minutes and with 15 µl EDTA-Na added and heated at 60° C. for 30 minutes with EDTA-Na added. All these sera were positive by the slide test as well as by the latex IgG tube technique.

Fifty percent of these sera (diluted 1:10 in buffer) were negative by latex IgG photometry. This inhibition was due to inhibition of RF by the $C_1$ component of the complement. By the use of heat and salt the $C_1$ complement component is dissociated and RF is released to react with latex IgG The $C_1$ component is dissociated into $C_{1q}$, $C_{1r}$ and $C_{1s}$ and the agglutination of $C_{1q}$ with latex particles may be prevented while using heat at 60° C. for 30 minutes with added 15 µl 0.1M EDTA-Na. The results were as follows:

|                               | Unheated No Salt 50% | Heated 56° EDTA-Na 100% | Heated 60° EDTA-Na 100% |
| ----------------------------- | -------------------- | ----------------------- | ----------------------- |
| Percent specimen              |                      |                         |                         |
| Positive/Negative for RF      | Negative             | Positive                | Positive                |

Since 63°±1° C. for 3 minutes may decrease the avidity of RF for latex particles coated with IgG, temperatures of 60° C. for 30 minutes should be used for preventing the agglutination of $C_{1q}$ in latex IgG particles.

EXAMPLE 7

Serum was obtained from a patient suffering from a *Cryptococcus neoformans* infection. The blood culture was positive for *Cryptococcus neoformans*. The serum had a titer of 1:60 when tested by the slide latex agglutination test (Meridian Diagnostics). The patients serum was serially diluted with glycine buffer #2 and a titer of 1:120 was detected using the Meridian Diagnostics latex antibody test.

An aliquot of this serum was tested with latex particles alone. The serum did not agglutinate and a straight line was obtained in the photometer recorder. After 3 minutes in the photometer 20 µl 0.1M NaEDTA was added and a flocculation curve was obtained which was interpreted as being due to the presence of the $C_{1q}$ component of the serum. When an aliquot of the serum was heated at 63° C. for 3 minutes the Cryptococcus test in one specimen was positive but in latex alone was negative. This demonstrated that the serum heated at 63° C. for 3 minutes became specific for Cryptococcus antigen by preventing the interference of $C_{1q}$.

EXAMPLE 8

A 30 µl sample of serum depleted of $C_1$ is modified by adding 30 µl of purified $C_{1q}$ and Cryptococcus polysaccharide (0.1 mg/ml) to form a test mixture. One aliquot of the mixture is tested on uncoated latex and latex coated with Cryptococcus antibody. A second aliquot is heated at 63° C. for 3 minutes prior to testing on the uncoated latex and the Cryptococcus latex. The results are as follows:

TABLE 6

|                                                                                                                                          | Latex (Uncoated) | Latex Cryptococcus |
| ---------------------------------------------------------------------------------------------------------------------------------------- | ---------------- | ------------------ |
| 25 µl $C_{1q}$ depleted serum with 30 µl $C_{1q}$ (0.5 mg/ml) unheated and 30 µl of Cryptococcus polysaccharide (0.1 mg/ml)              | 0.60             | 0.60               |
| 25 µl $C_{1q}$ depleted serum with 30 µl $C_{1q}$ (0.5 mg/ml) heated and 30 µl of Cryptococcus polysaccharide (0.1 mg/ml)                | 0                | 0.70               |

This example demonstrates that heat at 63° C. for 3 minutes will prevent $C_{1q}$ from agglutinating latex particles and that heat at 63° C. for 3 minutes will not affect the agglutination of Latex Cryptococcus antibody with Cryptococcus polysaccharide.

EXAMPLE 9

The invention also includes a novel apparatus for automatically carrying out immunoassays in which it is desired to inactivate $C_1$ or $C_{1q}$ in a sample of body fluid.

The apparatus may be used for:
1. Screening methodology for confirming that $C_{1q}$ has been inactivated.
2. Screening methodology for detection of $C_{1q}$ in any body fluid.
3. Screening methodology for confirming the presence of RF in a specimen of body fluid.
4. Methodology to demonstrate the absence of RF in a body fluid after treatment with mercaptoethanol.
5. Screening methodology for detection of RF.
6. Methodology for obtaining RF titers in body fluids.
7. Methodology to quantitate the concentration of RF (IgM) in body fluids.
8. Methodology to detect bacterial, fungal, parasitic, rickettsial and virus diseases using latex agglutination in an apparatus which eliminates $C_1$ and $C_{1q}$ form the sample of body fluid.

Figure 3:
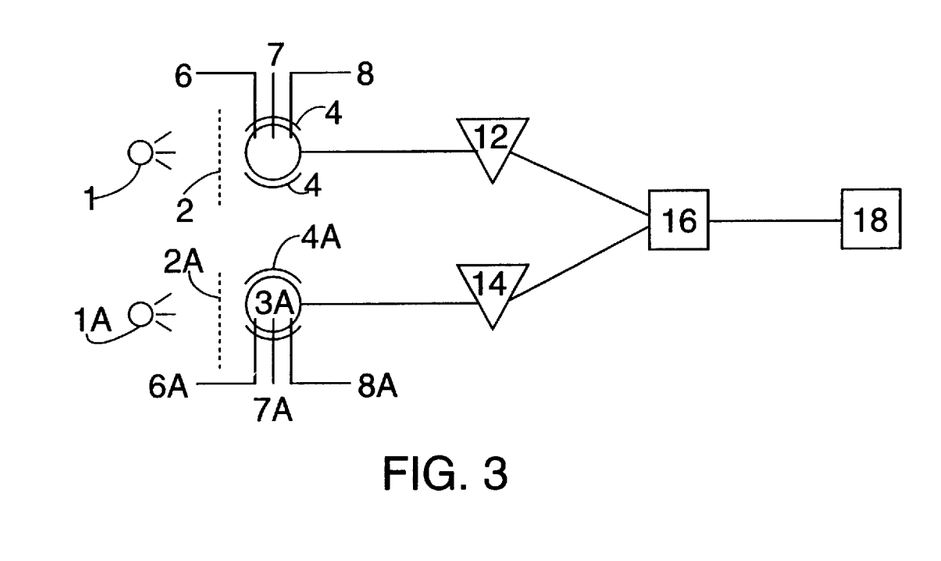
FIG. 3 is a schematic of an apparatus according to the invention.

FIG. 3 shows a schematic diagram of an apparatus of the invention. The basic structure of the invention comprises an irradiation unit comprising a light source 1; a filter or prism 2; a sample cell 3 for holding a sample of body fluid; an electronically controlled variable electric heater block 4 in proximity to cell 4 which is adapted to hold a test sample tube. The electronic control on the heater block 4 is capable of providing temperatures which will heat the sample in sample cell 3 to a temperature in the range of about 59°–64° C. for periods of time ranging from 3 minutes to 30 minutes or longer. The sample cell 3 has a number of associated reagent feed lines 6, 7 and 8 which are provided with automatic metering valves which are electronically controlled to deliver the required amounts of dispersed latex particles, chemical solution, and/or antigen or antibody solution, and/or mercaptoethanol solution. As shown in FIG. 3 line 6 is provided for delivering the dispersion of latex particles, line 7 is provided for the delivery of a neutral salt solution such as 2M NaCl and line 8 is provided for delivery of mercaptoethanol solution for immunoassays in which it desired to eliminate RF from the sample of body fluid. Reference cell 3A with light source 1A is provided for holding a control sample for compensation. Heater 4A and lines 6A, 7A and 8A are provided in the event it is desired to run a parallel control. Photocells 12 and 14 are placed in such a way that they will sense the light transmitted through the cells 3 and 3A. An amplifier 16 is used to amplify the signals from the photocells 12 and 14. The signals are sent to interface 18 and are processed in a computer for display on a CRT and/or printer which are not shown in FIG. 3. Cells 3 and 3A are preferably equipped with conventional magnetic stirrers which are utilized to keep the components of the test cell in suspension.

The novel apparatus of the invention may be operated as follows: an analyte such as sera (diluted with glycine buffer #2–1:10), which is to be tested for *Cryptococcus neoformans* is placed in the cell 3 and 10 μl of a 2M solution of KCl in water is metered into cell 3 through line 6. Heater block 4 is energized and the temperature of the cell is raised to 63° C. for three minutes to inactivate the $C_1$ and $C_{1q}$.

Thereafter, 15 μl of a dispersion of latex particles coated with *Cryptococcus neoformans* antibody is metered into cell 3 through line 6 while the magnetic stirrer is run at 1000 rpm. The change in optical density is then compared with a control which is run in cell 3A to determine if flocculation has occured. The detection of flocculation is read as a positive result for the presence of *Cryptococcus neoformans* antigen.

The apparatus of the invention may possess the basic structure of prior art photometric devices such as the Chronolog Model 570VS for performing optical aggregation tests. This apparatus may be modified to include a variable heater block means and associated timer means as well as reagent feed means which have been described herein. Suitable photometers which may be modified to embody the invention are described in U.S. Pat. No. 4,118,192, which is incorporated herein by reference or photometers which are commercially available such as the LA-2000 which is manufactured by Eiken Chemical Co.

OUCHTERLONY ANALYSIS

Confirmatory experiment for the effect of salts and heat for inactivation of $C_{1q}$ in human sera.

In the double diffusion agarose Ouchterlony technique the antibody or the antigen are applied to the center of the well and antigen or antibody are applied to 5 wells situated at the periphery of the plate. To each well is applied 10 μl of the material to be tested and 10 μl of antisera. The presence or absence of a precipitin line between antigen and antibody is read after the plates are kept at room temperature or in a refrigerator for 24 to 48 hours.

The following reagents were used for these series of experiments: Purified $C_{1q}$ conc. 0.04 mg/ml obtained from Diamedix Corp; Purified $C_{1q}$ conc. 0.5 mg/ml obtained from Diamedix Corp. Cytotec and Sigma; antisera to human $C_{1q}$ in goats was obtained from Sigma and Atlantic labs. Negative sera were obtained from heathly blood donors and rheumatoid sera from patients who were diagnosed as having rheumatoid arthritis. The salt was 1M Nacl.

Experiment A

Ten normal sera were tested. Normal sera were applied to the center well and 3 different antibodies were applied to the outer wells: (a) antibody to $C_{1q}$; (b) antibody to $C_{1r}$, and (c) antibody to $C_{1s}$; all antibodies precipitated at the mid-distance between the center well and outer well and the three line fused together.

Experiment B

Ten rheumatoid sera were studied by the same procedure as Experiment A and the same results were obtained.

Experiments A and B demonstrate clearly that normal serum and rheumatoid factor containing sera contains those proteins called $C_{1q}$, $C_{1r}$ and $C_{1s}$. The fact that they fuse together indicates that they are part of the same molecule which is $C_1$.

Experiment C

Purified $C_{1q}$, $C_{1r}$ and $C_{1s}$ preparations were tested according to the technique of Example 10 with their respective antisera and showed the same three precipitin lines which were observed in Example 11. This shows that $C_{1q}$, $C_{1r}$ and $C_{1s}$ react the same as $C_1$.

Experiment D

To 10 normal sera were added 10 μl of 0.1M EDTA tetrasodium according to the technique of Example 10. These samples and were heated at 56° C. for 30 minutes and tested with antisera to $C_{1q}$; all antisera gave a distinct precipitin line after 24 hours incubation demonstrating that the addition of a neutral salt and heat at 56° for 30 minutes enhances the $C_{1q}$ antigen precipitin line.

EXAMPLE 10

This examples is a method for the demonstration of the presence of $C_{1q}$ in sera and the use. The Methodology utilized for preparing the latex particles has been described in PROCEDURE A.

Material:

Ouchterlony diffusion on plate. In each of 6 tubes was:
1. 50 μl of a normal serum;
2. 50 μl of normal sera with added 30 μl of $Na_4$-EDTA;
3. 50 μl of rheumatoid sera with aded 30 μl of $Na_4$-EDTA;
4. 50 μl of normal sera with added 30 μl of $Na_4$-EDTA and heated at 60° C. for 30 minutes;
5. 50 μl of normal serum with added 30 μl of $Na_4$-EDTA and heated at 63° C. for 3 minutes. These sera in increments of 10 μl are added to the 6 outer well. In the outer well 10 μl of an antibody to $C_{1q}$ produced in rabbits or goats are added. Plates are incubated at room temperature for 24 and 48 hours. Precipitin lines are obtained from unheated normal sera, sera heated at 56° C. for 30 minutes and for normal and rheumatoid sera to which EDTA-$Na_4$ were added. Heating sera at 60° C. for 30 minutes and 63° C. for 3 minutes with the addition of salt prevented the development of precipitin lines.

EXAMPLE 11

This experiment illustrates the effect of temperature on the $C_{1q}$ molecule which in purified form is thermolabile at 56° C. for 30 minutes but thermostable at that temperature when complexed with $C_{In}$ or in sera when heated for 10–30 minutes.

TABLE 5

| | | | |
|---|---|---|---|
| 1* | 25 μl Normal serum unheated | ppt | ppt |
| 2* | 25 μl Normal serum heated at 56°C. for 30 minutes with 15 μl of 2M NaCl | ppt | ppt |
| 3* | 25 μl Normal serum heated at 56° 30 minutes with 15 μl of 2M NaCl | no ppt | very weak ppt |
| 4* | 10 μl $C_{1q}$/5 mg/ml | ppt | no ppt |
| 5* | 10 μl $C_{1q}$ heated at 56° C. for 30 minutes | no ppt | no ppt |
| 6* | 10 μl $C_{In}$ | no ppt | ppt |
| 7* | 10 μl $C_{1q}$ + 10 μl $C_{In}$ | ppt | ppt |
| 8* | 10 μl $C_{1q}$ + 10 μl $C_{In}$ heated at 56° C. for 10 minutes | ppt | ppt |
| 9* | 10 μl $C_{1q}$ + 10 μl $C_{In}$ heated at 56° C. for 20 minutes | ppt | ppt |
| 10* | 10 μl $C_{1q}$ + 10 μl $C_{In}$ heated at 56° C. for 30 minutes | ppt | ppt |
| 11* | 10 μl $C_{1q}$ + 10 μl $C_{In}$ heated at 63° C. for 3 minutes | no ppt | ppt |

*Control

The $C_{1r}$ inhibitor had 10 International Units (Calbiochem).

The invention is illustrated by Run No. 3 which shows that in the presence of a neutral salt, the $C_{1q}$ in serum is thermolabile at a temperature of 63° C. for 3 minutes while it is not thermolabile at a temperature of 56° C. for 30 minutes in the presence of a neutral salt.

EXAMPLE 12

To a 0.75 ml of a solution of human gamma globulin, 0.50 percent solution of 0.25 ml of glycine buffer No. 2 is added to six test tubes.

To each of the tubes are added:
1. Control+(HgG solution) 25 μl of buffer no. 2;
2. 25 μl of 2M NaCl;
3. 25 μl of $C_{1q}$ purified (0.5 mg/ml);
4. 25 μl $C_1$ purified (0.004 mg/ml);
5. 25 μl of $C_{1r}$ purified; and
6. 25 μl of $C_{1s}$ purified.

All tubes are incubated in a water bath at 64° C. 5–30 minutes. In this experiment turbidometric readings are made in the photometer and no latex particles are used.

The control tube and the tube containing human gamma globulin and $C_{1r}$ and $C_{1s}$ develop strong turbidity in about 5 minutes time; all other tubes which contain 2M NaCl, $C_{1q}$ and $C_1$ added to IgG did not develop any turbidity and appeared as clear as the original IgG unheated solution even when heated up to 30 minutes.

These experiments demonstrate that immunoglobulins heated at 64° C. for about 5 minutes develop aggregation. It also demonstrates that formation of aggregates by heat is prevented by the addition of neutral salt as well by $C_{1q}$ or $C_1$ to IgG previous to heating at 64° C.

The invention also includes kits for the carrying out of an immunoassay.

The kits of the invention may comprise the components of any conventionally available kit and (a) a chemical agent which when added to a sample of body fluid is capable of inactivating the $C_1$ or $C_{1q}$ in said body fluid when a mixture of said body fluid and said chemical compound are heated to a temperature of 59°–62° C. for a sufficient period of time to inactivate said $C_1$ and $C_{1q}$ without affecting the reactivity of an antigen or antibody in said body fluid and (b) a solution containing $C_{1q}$.

The kits of the invention may comprise the components of any conventionally available kit and (a) a chemical agent which when added to a sample of body fluid is capable of inactivating the $C_1$ or $C_{1q}$ in said body fluid when a mixture of said body fluid and said chemical compound are heated to a temperature of 59°–64° C. for a sufficient period of time to inactivate said $C_1$ and $C_{1q}$ without affecting the reactivity of an antigen or antibody in said body fluid and (b) a solution containing $C_{1q}$.

Examples of these kits are as follows:

1. Reagents used for the elimination of the interference of the $C_{1q}$ complement subcomponent of $C_1$ in fluid or sera:
   (a) antigen;
   (b) antibody;
   (c) control for antibody;
   (d) control for antigen;
   (e) a neutral salt (preferably 2M NaCl); and
   (f) buffer for antigen antibody reaction.

2. For in vitro diagnostic use, a kit will contain reagents used in the respective immunoassay procedures:
   (a) latex antigen or antibody emulsion;
   (b) latex antigen control;
   (c) latex rheumatoid factor control;
   (d) latex antibody control; and
   (e) a neutral salt (preferably 2M NaCl).

3. For RF identification and $C_{1q}$ screening technique:
   (a) latex particles solution 0.70–0.90 microns dia;
   (b) HGG 2%;
   (c) Glycine buffer solution pH 8.2, N=0.1;
   (d) RF purified protein;
   (e) RF serum standard;
   (f) Ouchterlony plate (optional);
   (g) purified $C_{1q}$;
   (h) neutral salt 2M NaCl or 2M KCl; and
   (i) mercaptoethanol solution 5M in $H_2O$.

Figure 2:
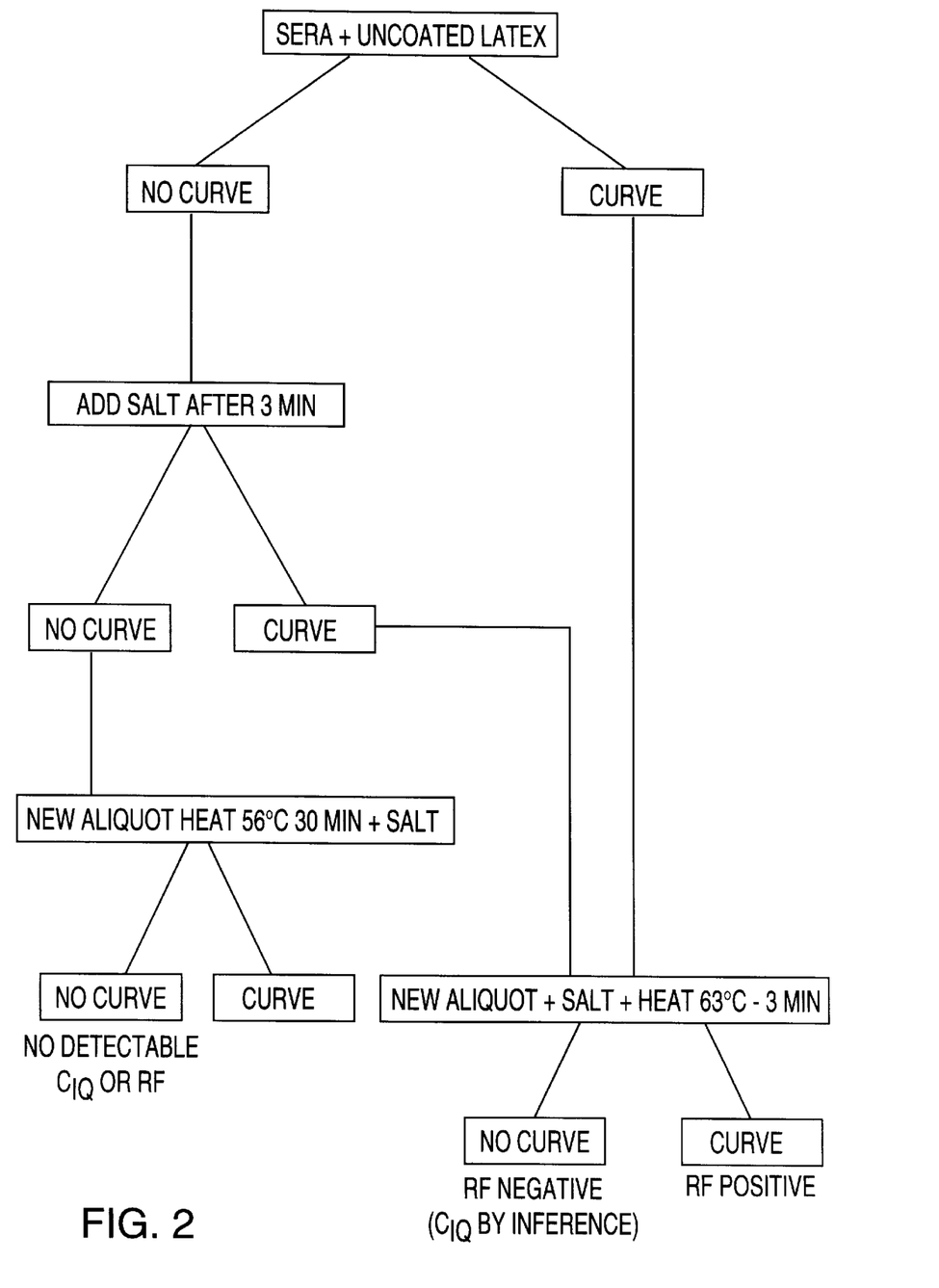
FIG. 2 is a flow chart which shows the sequence of steps for the screening method of the invention for determining if a body fluid is RF positive or contains $C_{1q}$.

FIG. 2 is a flow chart which provides a step by step sequence of steps that will enable the determination of the presence of RF or $C_{1q}$ in a sample of serum. The chart sets forth the steps to be followed if a particular test provides a particular result. The chart describes how to distinguish between the latex flocculation produced by $C_{1q}$ and RF.

I claim:

1. A method for preventing interference caused by $C_1$ or $C_{1q}$ in an immunoassay of a body fluid for an antigen or an antibody, said method comprising heating a sample of said body fluid, which is diluted sufficiently to permit an immunoassay, to a temperature of 59° C. to 64° C. with a neutral salt for a period of time sufficient for said neutral salt to prevent said interference caused by said $C_1$ or $C_{1q}$ without affecting said antigen or said antibody in said immunoassay.

2. The method as defined in claim 1, wherein the body fluid is serum.

3. The method as defined in claim 1 wherein the heating is carried out at 63° C. for 3 minutes.

4. The method as defined in claim 1 when the neutral salt is sodium chloride.

5. The method as defined in claim 1 wherein the diluted body fluid is serum diluted 1:10.

6. The method as defined in claim 1 wherein the neutral salt is selected from the group consisting of sodium chloride and ethylene diamine tetraacetic acid, tetrasodium salt.

7. A method for preventing increased formation of aggregates of immunoglobulin in a body fluid while inactivating $C_{1q}$ in said body fluid, said method comprising heating a sample of said body fluid, which is sufficiently diluted to permit an immunoassay, to a temperature of 59° C. to 64° C. with a neutral salt for a period of time to inactivate said $C_{1q}$ without causing said increased formation of said aggregates of said immunoglobulin.

8. The method as defined in claim 7 when the neutral salt is sodium chloride.

9. The method as defined in claim 7 wherein the diluted body fluid is serum diluted 1:10.

10. A method for detecting rheumatoid factor (RF) in a body fluid comprising immunoreactive antigens and antibodies, said method comprising:
   (a) diluting a first aliquot of a body fluid 1:10 with a pH 8.2 glycine buffer and contacting thereto a first suspension of uncoated latex particles, wherein a lack of flocculation after three minutes indicates the absence of said RF,
   (b) if said (a) results in flocculation,
      (1) heating a second aliquot of said body fluid diluted 1:10 with said pH 8.2 glycine buffer to a temperature of 59° C. to 64° C. with a neutral salt for 3 to 30 minutes such that said neutral salt inactivates any $C_{1q}$ present in said body fluid without affecting the immunoreactivity of said antigens or said antibodies to form a heat treated sample, and
      (2) contacting said heat treated sample with a suspension of said uncoated latex particles, wherein any resultant flocculation indicates the presence of RF in said body fluid.

11. The method as defined in claim 10 when the neutral salt is sodium chloride.

12. A method for preventing interference caused by $C_1$ or $C^{1q}$ in a latex particle photometric immunoassay of a body fluid for an antigen or an antibody, said method comprising heating a sample of said body fluid, which is diluted sufficiently to permit an immunoassay, to a temperature of 59° C. to 64° C. with a neutral salt for a period of time sufficient for said neutral salt to prevent said interference caused by said $C_1$ or $C_{1q}$ without affecting said antigen or said antibody in said latex particle photometric immunoassay.

* * * * *